US009278053B2

(12) United States Patent
Moore et al.

(10) Patent No.: US 9,278,053 B2
(45) Date of Patent: Mar. 8, 2016

(54) APPARATUS AND SYSTEM WITH PRE-LOADED CASSETTE FOR DISPENSING MULTIPLE MEDICATIONS AND METHODS THEREFORE

(71) Applicant: Xerox Corporation, Norwalk, CT (US)

(72) Inventors: Steven R. Moore, Pittsford, NY (US); Paul R. Austin, Webster, NY (US); Linn C. Hoover, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 240 days.

(21) Appl. No.: 14/080,039

(22) Filed: Nov. 14, 2013

(65) Prior Publication Data
US 2015/0134108 A1    May 14, 2015

(51) Int. Cl.
*A61J 7/04*    (2006.01)
*G06F 19/00*    (2011.01)

(52) U.S. Cl.
CPC ............. *A61J 7/0481* (2013.01); *A61J 7/0427* (2015.05); *A61J 7/0445* (2015.05); *A61J 7/0454* (2015.05); *G06F 19/3462* (2013.01); *A61J 2200/30* (2013.01)

(58) Field of Classification Search
CPC ... A61J 2220/30; A61J 7/0481; A61J 7/0427; A61J 7/0445; A61J 7/0454; G06F 19/3462
USPC ................................................. 700/231–244
See application file for complete search history.

(56) References Cited

U.S. PATENT DOCUMENTS

| | | | |
|---|---|---|---|
| 5,971,594 A * | 10/1999 | Sahai et al. | 700/242 |
| 6,294,999 B1 * | 9/2001 | Yarin et al. | 340/573.1 |
| 6,529,446 B1 * | 3/2003 | de la Huerga | 368/10 |
| 6,611,733 B1 * | 8/2003 | De La Huerga | 700/236 |
| 6,662,081 B1 | 12/2003 | Jacober et al. | |
| 6,702,146 B2 * | 3/2004 | Varis | 221/3 |
| 7,044,302 B2 * | 5/2006 | Conley | 206/538 |
| 7,543,718 B2 * | 6/2009 | Simon | 221/13 |
| 7,711,449 B2 | 5/2010 | Abdulahy et al. | |
| 7,743,923 B2 * | 6/2010 | Conley | 206/534.1 |
| 8,214,077 B2 | 7/2012 | Bertrand et al. | |
| 2002/0147526 A1 * | 10/2002 | Siegel | 700/237 |
| 2013/0066463 A1 * | 3/2013 | Luoma et al. | 700/232 |

* cited by examiner

*Primary Examiner* — Patrick Cicchino
(74) *Attorney, Agent, or Firm* — Simpson & Simpson, PLLC (57) ABSTRACT

An apparatus for dispensing medications, including: a dispensing device storing prescription information including: identification of each medication included in a first plurality of medications; a respective dosage for each medication; and a plurality of time spans, including respective points in time, for dispensing the first plurality of medications; a cassette installed in the dispensing device and including a plurality of sealed compartments, each compartment in the plurality of sealed compartments configured to store at least one respective pill for each medication in a second plurality of medications; and at least one dispensing port. The dispensing device is configured to, within each time span in the plurality of time spans and when the second plurality of medications is in compliance with the prescription information: access each compartment via the at least one dispensing port; and extract every at least one first pill from each compartment.

27 Claims, 7 Drawing Sheets

APPARATUS AND SYSTEM WITH PRE-LOADED CASSETTE FOR DISPENSING MULTIPLE MEDICATIONS AND METHODS THEREFORE

TECHNICAL FIELD

The present disclosure relates to an apparatus with a pre-loaded cassette including a plurality of compartments in which are stored a plurality of medications. The cassettes are sealed and the apparatus is configured to extract, from each compartment, the medications according to a schedule. The present disclosure also includes a computer-based system including a computer for a service entity configured to receive prescriptions from health care providers, transmit the prescriptions to a pharmacy entity, which loads the medications in the compartments, and communicate with the apparatus.

BACKGROUND

Medication adherence, including patient adherence to medication regimens is an important aspect of any system providing medical services. Specifically, lack of medical adherence has a negative effect on outcomes and increases costs associated with providing medical services. For example, research shows that:

1. Approximately 25% of patients prescribed medications for a new illness fail to fill their initial prescription;
2. Approximately half of patients taking maintenance medications for a chronic disease stop taking their medications within the first year; and,
3. The estimated cost of unnecessary medical treatment attributable to medication non-adherence is $290B annually.

Several solutions have been proposed to address the problem of medical adherence with respect to medication regimens. One solution path is to provide more coordinated delivery of medications to the patient, especially since many people have prescriptions for multiple medications, each requiring different dosage regimens. For example, it is known for a pharmacy to deliver multiple medications by mail in blister-pack format. Each blister in the package contains all medications to be taken at one time. There may be two to four blisters per day. Each package will typically contain a week's worth of a patient's medications. The patient is required to burst the appropriate blister at the appropriate time, remove the pills, and take them. However, there are known problems with this approach. For example, the medication administration is 'open loop', that is, there is no way for a health care provider, pharmacy, or other interested party to determine of if the pills were removed from a blister at the appropriate time and taken by the patient at the appropriate time. The blister pack must be amenable to handling and shipping, for example, relatively inexpensive, light weight, and easy filled. However, such a configuration may not be an optimal configuration for a patient to use.

It is also is known to use home-based medication dispensers. For example, the patient or a designated caregiver is required to periodically pre-load the appropriate pills into provided cups, according to each pill's dosage regimen. The pre-loaded cups are then placed into the dispenser. The dispenser then releases each cup's contents at a designated time. The dispenser, being an active device, can alert the patient via audible alarm that medication is due to be taken. The dispenser can also communicate via telephone line with a remote caregiver or monitoring service. However, there are problems with the dispensers. The patient and/or caregiver must be responsible to fulfill multiple prescriptions, which may be out of synch with each other. Any pill packing errors by the patient or caregiver will not be detected by the dispenser. Any potential medication interactions will not be flagged since different prescriptions are not coordinated.

SUMMARY

According to aspects illustrated herein, there is provided an apparatus for dispensing medications, including: a dispensing device configured to store first prescription information including: an identification of each first medication included in a first plurality of medications; a respective dosage for each first medication; and a first plurality of time spans, including first respective points in time, for dispensing the first plurality of medications; a cassette installed in the dispensing device and including a first plurality of sealed compartments, each first compartment in the first plurality of sealed compartments storing at least one first respective pill for each medication in a second plurality of medications; and at least one dispensing port. The dispensing device is configured to, within each first time span in the first plurality of time spans and when the second plurality of medications is in compliance with the first prescription information: access each first compartment via the at least one dispensing port; and extract every at least one first pill from each first compartment. Sealing of the first plurality of sealed compartments prevents access to each first compartment except through the at least one dispensing port.

According to aspects illustrated herein, there is provided a method for dispensing medications, including: storing in a dispensing device first prescription information including: a respective identification of each first medication included in a first plurality of medications; respective dosages for each first medication; and first plurality of time spans, including first respective points in time, for dispensing the first plurality of medications; placing, in each first compartment in a first plurality of compartments for a cassette, at least one first respective pill for each medication in a second plurality of medications; sealing the first plurality of compartments; blocking access to each first compartment except through at least one dispensing port; installing the cassette in the dispensing device; within each first time span in the first plurality of time spans and when the second plurality of medications is in compliance with the first prescription information: accessing, using the dispensing device, each first compartment via the at least one dispensing port; and extracting, using the dispensing device, every at least one first pill from each first compartment.

According to aspects illustrated herein, there is provided a computer-based system for dispensing medications, including: a first computer, operated by or for a service entity, including a first processor and a first memory element configured to store first computer readable instructions; a second computer, operated by or for a pharmacy entity separate from the service entity, including a second processor and a second memory element configured to store second computer readable instructions; and a dispensing apparatus remotely located from the service entity and the pharmacy entity and including a dispensing device including a third computer with a third processor and a third memory element configured to store third computer readable instructions. The first processor is configured to execute the first computer readable instructions to: receive, from at least one first health care provider, a first plurality of prescriptions for a first plurality of medications, each prescription in the first plurality of prescriptions including: an identification of a first respective medication; a respective dosage for the first respective medication; and a first plurality of time spans, including first respective points in time, for dispensing the first plurality of medications; and transmit to the second computer the first plurality of prescriptions and instructions to place in each first compartment of a first plurality of compartments for a cassette, installable in the dispensing device, the first plurality of medications. The dispensing apparatus includes: the cassette, installed in the dispensing device, with the at least one first respective pill for each second medication included in a second plurality of medications; and at least one dispensing port. The cassette is sealed to block access to each first compartment except through the at least one dispensing port. The third processor is configured to execute the third computer readable instructions to: receive the first plurality of prescriptions; and within each first time span in the first plurality of time spans, and when the second plurality of medications is in compliance with the first plurality of prescription: access, using the dispensing device, each first compartment via the at least one dispensing port; and extract, using the dispensing device, every at least one first pill from each first compartment.

According to aspects illustrated herein, there is provided a computer-based method for dispensing medications, including: storing, in a first memory element of a first computer, operated by or for a service entity, first computer readable instructions; executing, using a first processor the first computer readable instructions to receive, from at least one first health care provider, a first plurality of prescriptions for a first plurality of medications, each prescription in the first plurality of prescriptions including: an identification of a first respective medication included in the first plurality of medications; a respective dosage for the first respective medication; and a first plurality of time spans, including first respective points in time, for dispensing the first respective medication and transmit to a second computer, operated for or by a pharmacy entity separate from the service entity the first plurality of prescriptions and instructions to place in each first compartment of a first plurality of compartments for a cassette, installable in the dispensing device, the first plurality of medications; placing, at a facility operated by or for the pharmacy entity, in each first compartment in a first plurality of compartments for a cassette, at least one first respective pill for each second medication in a second plurality of medications; sealing the cassette to block access to each first compartment except through at least one dispensing port; installing, in a dispensing apparatus including a third computer with a third processor and third memory element, the cassette, with the at least one first respective pill for each second medication present in each first compartment; storing third computer readable instructions in the third memory element; executing, using the third processor, the third computer readable instructions to receive the first plurality of prescriptions; and within each first time span in the first plurality of time spans, and when the second plurality of medications is in compliance with the first plurality of prescriptions: access, using a dispensing device included in the dispensing apparatus, each first compartment via the at least one dispensing port and extract, using the dispensing device, every at least one first pill from each first compartment.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Moreover, although any methods, devices or materials similar or equivalent to those described herein can be used in the practice or testing of these embodiments, some embodiments of methods, devices, and materials are now described.

Figure 1:
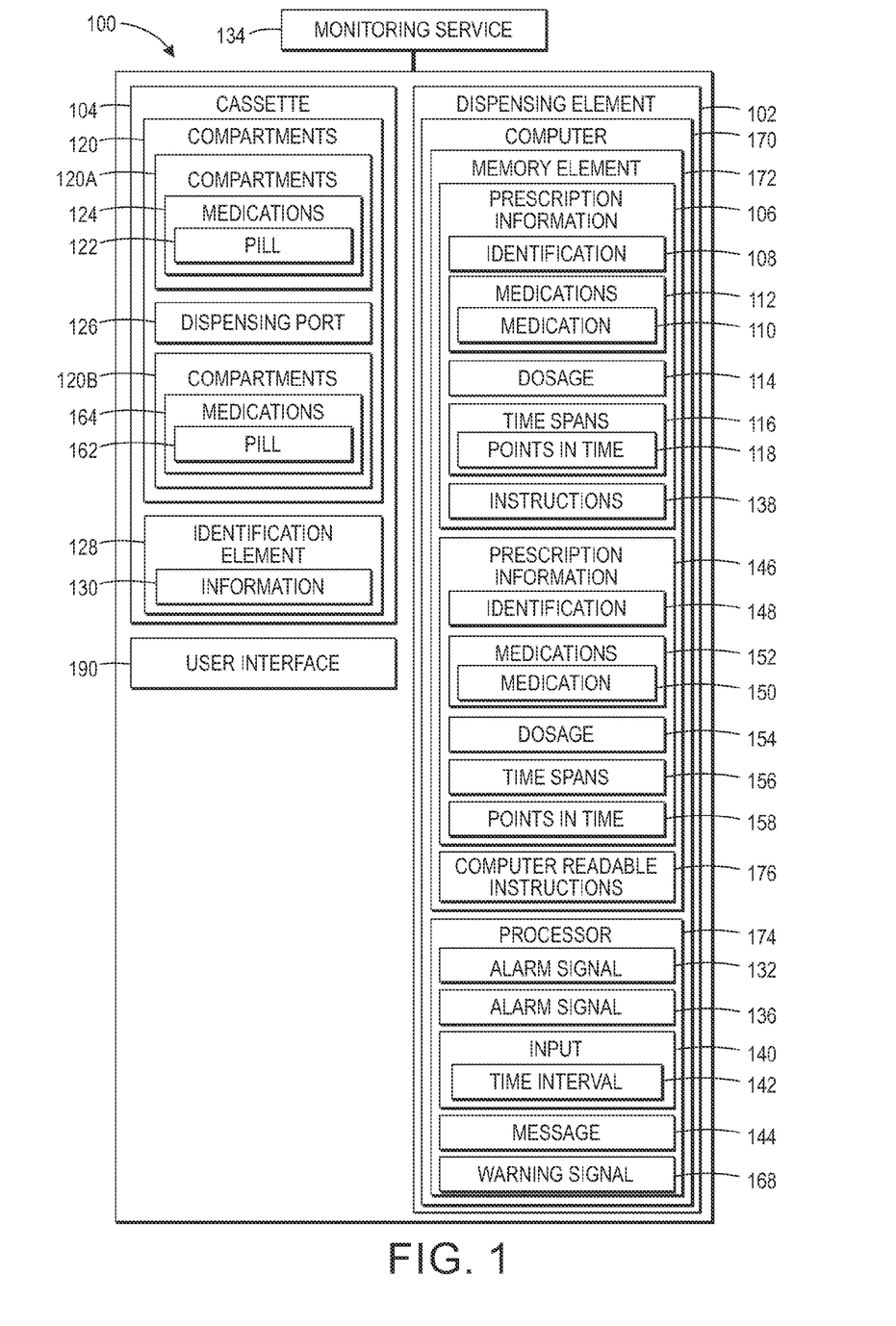
FIG. 1 is a schematic block diagram of an apparatus for dispensing medication; and, FIG. 2 is a schematic representation of a top view of an example cassette for the apparatus in FIG. 1.

FIG. 1 is a schematic block diagram of apparatus 100 for dispensing medication.

Figure 2:
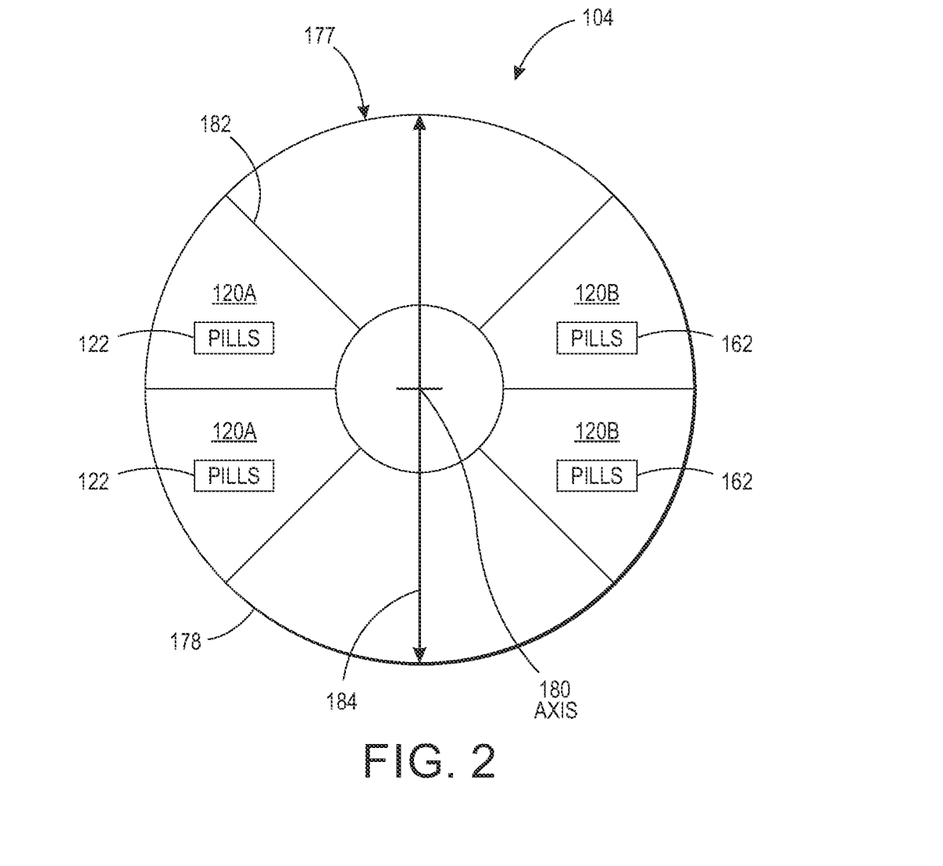

FIG. 2 is schematic representation of a top view of an example cassette for apparatus 100 in FIG. 1.

Figure 3:
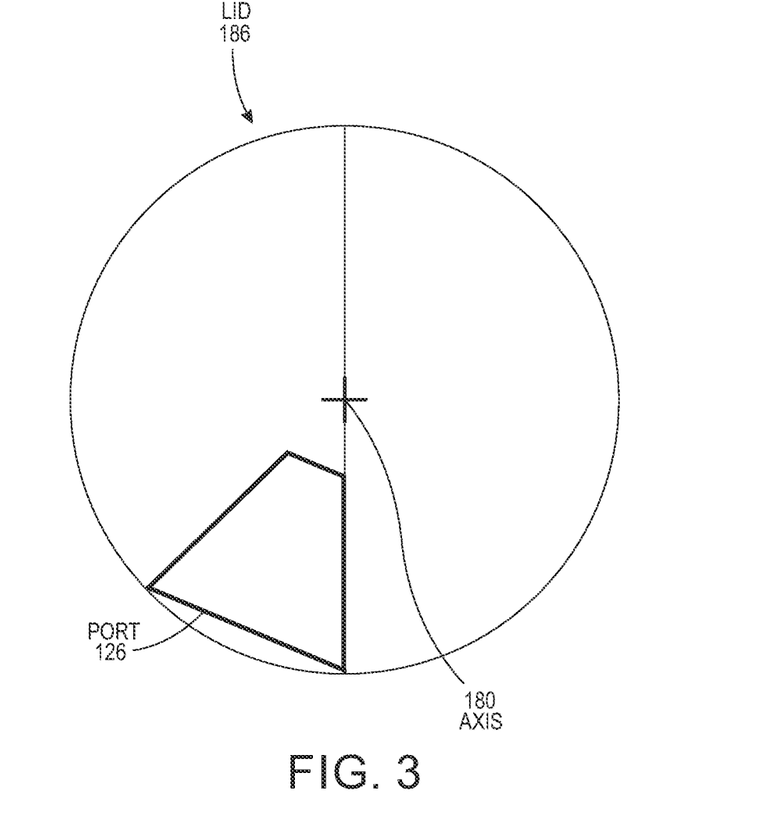
FIG. 3 is a schematic representation of a view of an example lid for an example cassette for the apparatus in FIG. 1.

FIG. 3 is schematic representation of a view of an example lid for an example cassette for apparatus 100 in FIG. 1. The following should be viewed in light of FIGS. 1 through 3. Apparatus 100 includes dispensing device 102 and cassette 104. Device 102 is configured to store prescription information 106 including identification 108 of each medication 110 included in medications 112. Information 106 also includes respective dosage 114 for each medication 110 and time spans 116 for dispensing medications 112. Each time span 116 includes a respective point in time 118. The cassette is installed in dispensing device 102 and includes sealed compartments 120. At least one compartment 120 is arranged to store at least one respective pill 122 for each medication included in medications 124. For example, each compartment 120A included in compartments 120 is arranged to store at least one respective pill 122 for each medication included in medications 124. By "pill" we mean any element known in the art comprising or for containing a medication, including, but not limited to solid pills of a compressed form of the medication or capsules containing the medication in powder, pellet, or liquid form. Apparatus 100 includes at least one dispensing port 126. The discussion that follows is directed to one port 126; however, it should be understood that other numbers of ports are possible. The sealing of compartments 120 prevents access to compartments 120 except through dispensing port 126. The sealing prevents unauthorized access to compartments 120 and ensures that the contents of the compartments are known and are not tampered with.

Each time span 116 specifies a particular time interval, for example, 10 minutes or one hour. Each point in time 118, for example, 8 AM or 7:30 PM, provides a context for the respective time span 116. For example, if point in time 118 is 8 AM and time span 116 is one hour, then time span 116 occurs with respect to 8 AM. Any relationship known in the art is possible between a time span 116 and the respective point in time 118. For example, if point in time 118 is 8 AM and time span 116 is one hour, the time span can begin or end on the point in time, the time span can be ½ hour before and after 8 AM, or a majority, but not all of the time span can be before or after 8 AM.

Dispensing device 102 is configured to, within each respective time span 116 and when medications 124 are in compliance with prescription information 106: access each compartment 120A via dispensing port 126 and extract pills 122 from the compartments.

In an example embodiment, cassette 104 includes identification element 128 storing prescription information 130 regarding medications 124 and dispensing device 102 is configured to determine, using prescription information 106 and 130, whether medications 124 are the same as medications 112 and are in compliance with prescription information 106. That is, whether the correct medications are stored in compartments 120A. Dispensing device 102 is further configured to access each compartment 120A via dispensing port 126 and extract pills 122 from the compartment within each time span 116 when medications 112 and medications 124 are the same and medications 124 are in compliance with prescription information 106. Compliance with prescription information 106 can include, but is not limited to: being the same medication as included in prescription information 106 and having the same dosages 114 as included in prescription information 106, or being the same medication as included in prescription information 106 and having the same time spans 116 as included in prescription information 106.

In an example embodiment, when dispensing device 102 determines that medications 124 are not the same as medications 112 or are not in compliance with prescription information 106, the dispenser is configured to block extraction of pills 122 from one or more compartments 120A, transmit alarm signal 132, and implement sensory alarm signal 136. Signal 136 can be any sensory alarm signal known in the art, including, but not limited to visual, auditory, or tactile. In an example embodiment, alarm signal 132 is a patient and/or caregiver contact event, such as an email, text, or phone call. In an example embodiment, signal 132 is transmitted to monitoring service 134 remote from apparatus 100.

In an example embodiment, prescription information 106 includes instructions 138 to extract pills from a particular compartment 120A, within a particular time span 116, for example time span 116A. The dispensing device is configured to receive input 140 and in response to input 140, abort, within time span 116A, dispensing of pills 122 from the compartment 120A and extract pills 122 from the compartment 120A prior to or after time span 116A. In an example embodiment, input 140 includes time interval 142 and the dispensing device is configured to extract pills 122 in the compartment 120A prior to or after point in time 118A, included in time span 116A, by an amount of time equal to time interval 142. In an example embodiment, dispensing device 102 is configured to determine if extracting pills 122 in the compartment 120A prior to or after point in time 118A by an amount of time equal to time interval 142 is in compliance with prescription information 106. If the extraction is not in compliance with prescription information 106, dispensing device 102 is configured to block extraction of pills 122 from compartment the 120A and transmit message 144 stating that the change in extraction time has been blocked.

In an example embodiment, the dispensing device is configured to store prescription information 146 including identification 148 of each medication 150 included in medications 152. Information 146 also includes respective dosage 154 for each medication 150 and time spans 156 for dispensing medications 152. Each time span 156 includes a respective point in time 158. The discussion regarding time spans 116 and points in time 118 is applicable to time spans 156 and points in time 158. At least one compartment 120 is arranged to store at least one respective pill 162 for each medication included in medications 164. For example, each compartment 120B included in compartments 120 is arranged to store at least one respective pill 162 for each medication included in medications 164. The sealing of compartments 120B prevents access to compartments 120B compartment except through dispensing ports 126. The sealing prevents unauthorized access to compartments 120B and ensures that the contents of the compartments are known and are not tampered with.

Dispensing device 102 is configured to, within each respective time span 156 and when medications 164 are in compliance with prescription information 146: access each compartment 120B via dispensing port 126 and extract pills 164 from the compartments.

In an example embodiment, the dispensing device is configured to determine that cassette 104 has not been installed in dispensing element 102 by point in time 166 and transmit warning signal 168. Signal 168 also can be triggered by a determination by dispenser element 102 that cassette 104 is empty or has only a predetermined number of compartments left storing medications. In an example embodiment, alarm signal 168 is a patient and/or caregiver contact event, such as an email, text, or phone call. In an example embodiment, signal 168 is transmitted to monitoring service 134.

In an example embodiment, the dispensing device is configured to determine that element 102 has extracted pills, for example pills 122, from a compartment 120, for example from a compartment 120A, and that the pills have not been removed from apparatus 100. In response to the preceding determination, the dispensing device transmits alarm signal 169. In an example embodiment, alarm signal 169 is a patient and/or caregiver contact event, such as an email, text, or phone call. In an example embodiment, alarm signal 169 is transmitted to monitoring service 134.

In an example embodiment, dispensing device 102 includes computer 170 with memory element 172 and processor 174. Element 172 is configured to store computer readable instructions 176 and prescription information 106. Processor 174 is configured to execute computer readable instructions 176 to, with each time span 116, and when medications 124 are in compliance with prescription information 106, access using element 102, each compartment 120A via dispensing port 126 and extract, using element 102, every pill 122 from the compartment.

Figure 4:
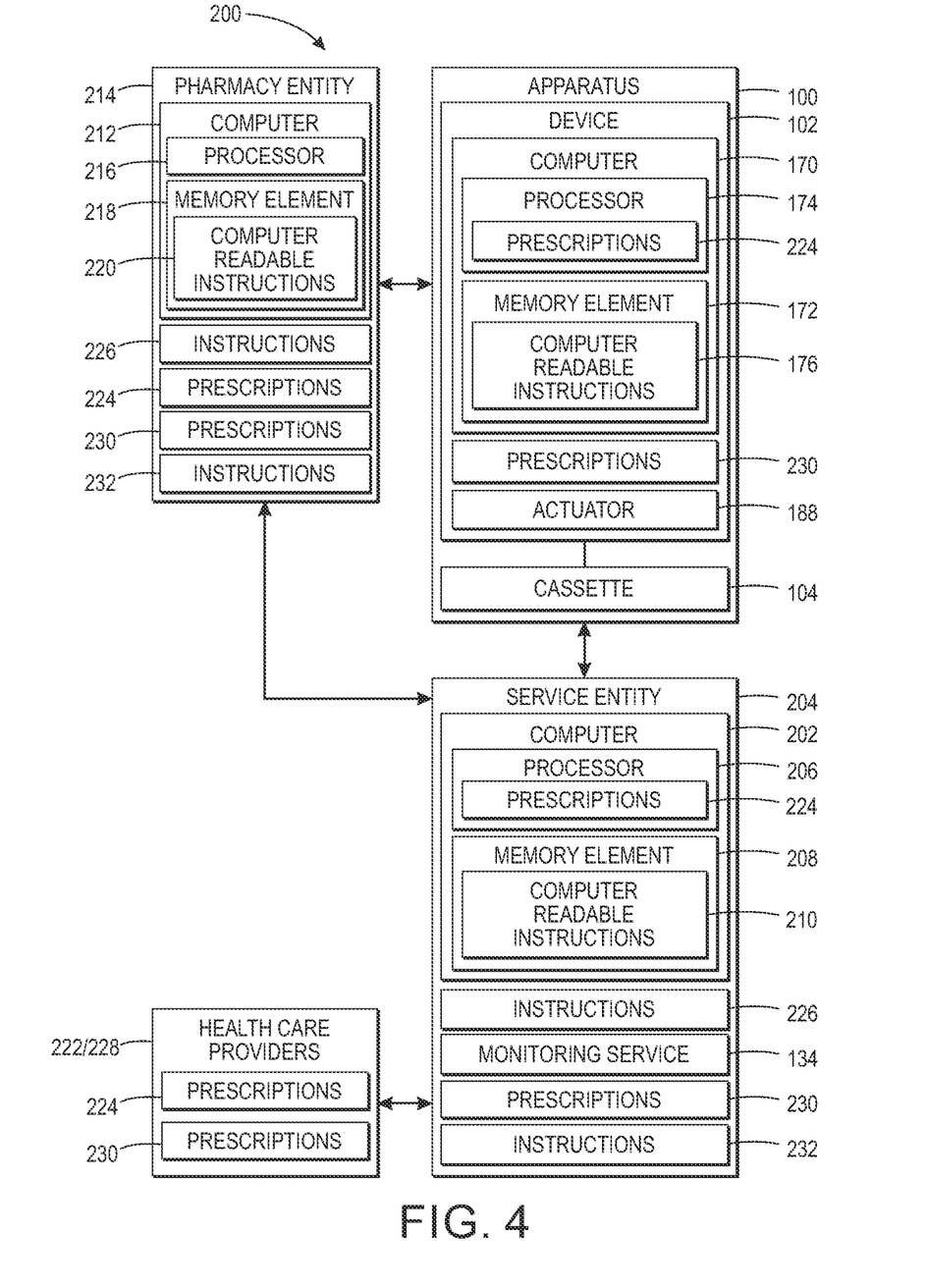
FIG. 4 is a schematic block diagram of a system for dispensing medication.

FIG. 4 is a schematic block diagram of system 200 for dispensing medication. The following should be viewed in light of FIGS. 1 through 4. Computer-based system 200 for dispensing medications includes computer 202 operated by or for service entity 204, processor 206, and memory element 208 configured to store computer readable instructions 210. System 200 includes computer 212, operated by or for pharmacy entity 214 separate from service entity 204. Computer 212 includes processor 216 and memory element 218 configured to store computer readable instructions 220. System 200 includes dispensing apparatus 100 remotely located from service entity 204 and pharmacy entity 214. Apparatus 100 includes dispensing device 102, cassette 104, and computer 166. Dispensing device 102 includes computer 170 with memory element 172 and processor 176. Memory element 172 is configured to store computer readable instructions 176.

Processor 206 is configured to execute computer readable instructions 210 to receive, from at least one health care provider 222, prescriptions 224 for medications 112. Each prescription 224 includes a respective identification 108 of each medication 110, a respective dosage 114 for each medication 110 and time spans 116 for dispensing medications 112. Processor 206 is configured to execute the computer readable instructions 210 to transmit, to computer 212: prescriptions 224; and instructions 226 to place in each compartment 120A medications 112. The pharmacy entity places medications 124 in compartments 120A in response to prescriptions 224 and seals compartments 120A. Processor 174 is configured to execute computer readable instructions 176 to receive prescriptions 224. Processor 174 is configured to execute computer readable instructions 176 to, within each respective time span 116 and when medications 124 are in compliance with prescription information 106: access, using element 102, each compartment 120A via dispensing port 126 and extract, using element 102, pills 122 from the compartments.

In an example embodiment, processor 206 is configured to execute the computer readable instructions 210 to transmit prescriptions 224 to computer 170.

In an example embodiment, processor 174 is configured to execute computer readable instructions 176 to determine, using prescription information 106 and 130, whether medications 124 are the same as medications 112 and are in compliance with prescription information 106. That is, whether the correct medications are stored in compartments 120A. Processor 174 is configured to execute computer readable instructions 176 to access, using element 102, each compartment 120A via dispensing port 126 and extract, using element 102, pills 122 from the compartment within each time span 116 when medications 112 and medications 124 are the same and medications 124 are in compliance with prescription information 106.

In an example embodiment, at least one health care provider 222 includes a plurality of health care providers.

In an example embodiment, processor 174 is configured to execute computer readable instructions 176 to determine that medications 124 are not the same as medications 112 or are not in compliance with prescription information 106. Processor 174 is configured to execute computer readable instructions 176 to block extraction, using element 102, of pills 122 from one or more compartments 120A, transmit alarm signal 132, and implement sensory alarm signal 136. In an example embodiment, monitoring service 134 is included in service entity 204.

In an example embodiment, processor 174 is configured to execute computer readable instructions 176 to receive input 140 and in response to input 140, abort, within time span 116A, dispensing of pills 122 from a particular compartment 120A and extract, using element 102, pills 122 from the particular compartment 120A prior to or after time span 116A. In an example embodiment, processor 174 is configured to execute computer readable instructions 176 to determine if extracting pills 122 from the particular compartment 120A prior to or after point in time 118A by an amount of time equal to time interval 142 is in compliance with prescription information 106. If the extraction is not in compliance with prescription information 106, processor 174 is configured to execute computer readable instructions 176 to block extraction of pills 122 from the particular compartment 120A and transmit message 144 stating that the change in extraction time has been blocked.

In an example embodiment, processor 206 is configured to execute the computer readable instructions 210 to receive, from at least one health care provider 222 or at least one health care provider 228 prescriptions 230 for medications 152. Each prescription 230 includes a respective identification 148 of each medication 150 included in medications 152, a respective dosage 154 for each medication 150 and time spans 156 for dispensing medications 152. Processor 206 is configured to execute the computer readable instructions 210 to transmit, to computer 212: prescriptions 230; and instructions 232 to place medications 152 in each compartment 120B. The pharmacy entity places medications 164 in compartments 120B in response to prescriptions 228 and seals compartments 120B. Processor 174 is configured to execute computer readable instructions 176 to receive prescriptions 228. Processor 174 is configured to execute computer readable instructions 176 to, within each respective time span 156 and when medications 164 are in compliance with prescription information 106: access, using element 102, each compartment 120B via dispensing port 126 and extract, using element 102, pills 162 from the compartments.

In an example embodiment, Processor 174 is configured to execute computer readable instructions 176 to determine that element 102 has extracted pills, for example pills 122, from a compartment 120, for example from a compartment 120A, and that the pills have not been removed from apparatus 100. In response to the preceding determination, processor 174 is configured to execute computer readable instructions 176 to transmit alarm signal 169. In an example embodiment, alarm signal 169 is a patient and/or caregiver contact event, such as an email, text, or phone call. In an example embodiment, alarm signal 169 is transmitted to monitoring service 134.

Figure 5:
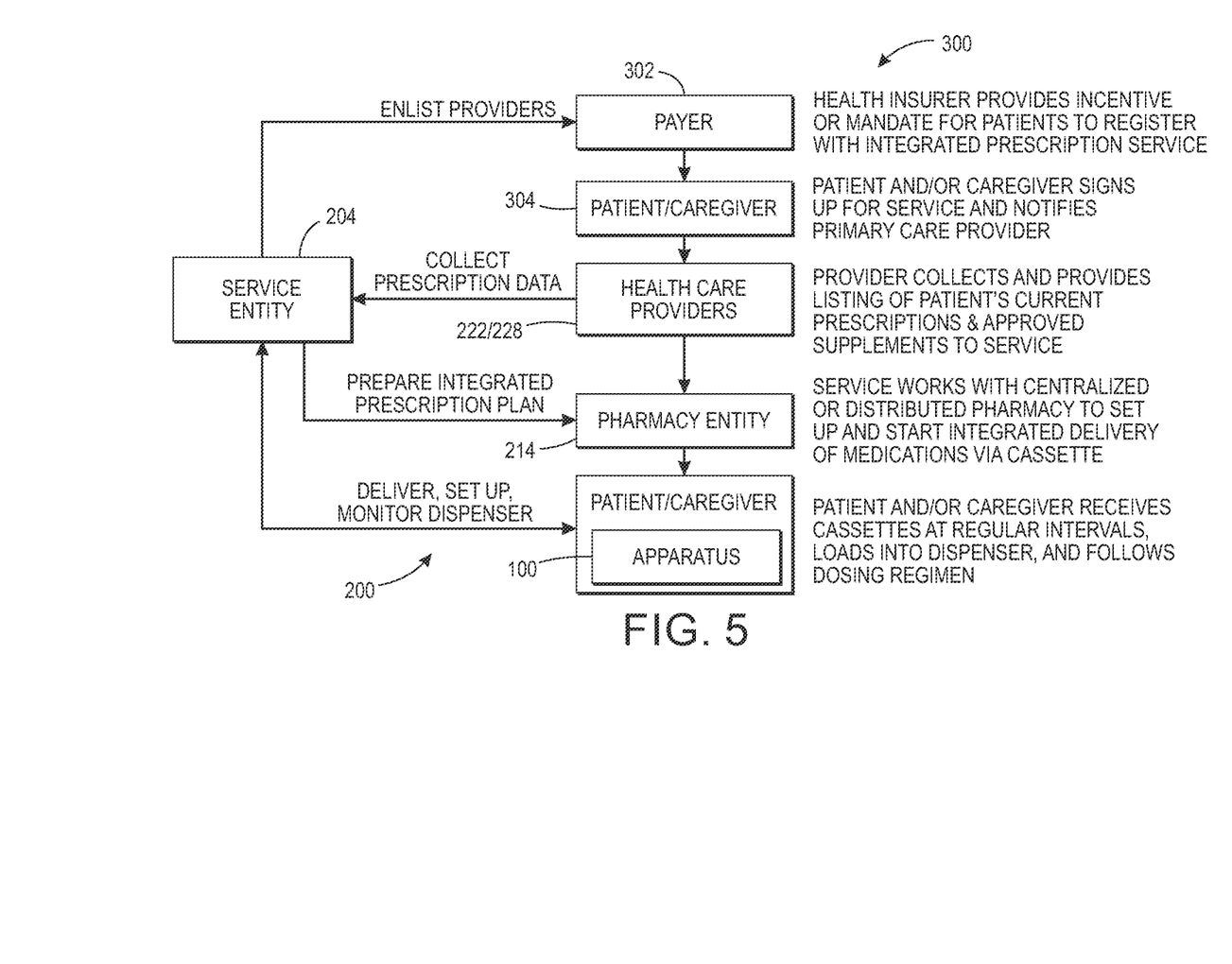
FIG. 5 depicts a flow chart of a system for dispensing medication.

FIG. 5 depicts flow chart 300 of a system for dispensing medication. FIG. 5 is an example of A process for controlling dispensing of medications using system 200. The discussions regarding apparatus 100 and system 200 are applicable to FIG. 5. In FIG. 5, payer 302 and patient/caregiver 304 have been added to system 200. As noted above, lack of adherence to medication regimens results in poor outcomes for patients and increased costs. These increased costs are borne by the patient, for example, patient 304 and the payer, for example payer 302. Payer 302 can be a private health care insurance provider or a government administrated program such as Medicare or Medicaid. Advantageously, system 200 enables better adherence to medication regimens, which in turn improves outcomes and reduces costs for patient 304 and reduces costs for payer 302.

The discussions above and below directed to information 106, medications 112, and compartments 120A are applicable to information 146, medications 152, and compartments 120B. It also should be understood that apparatus 100 is not limited to the two sets of prescription information, medications, and compartments described above, and that other numbers of sets of prescription information, medications, and compartments are possible. It also should be understood that although sets of prescription information, medications, and compartments described above, the descriptions above are applicable to a single sets of prescription information, medications, and compartments.

Figure 6:
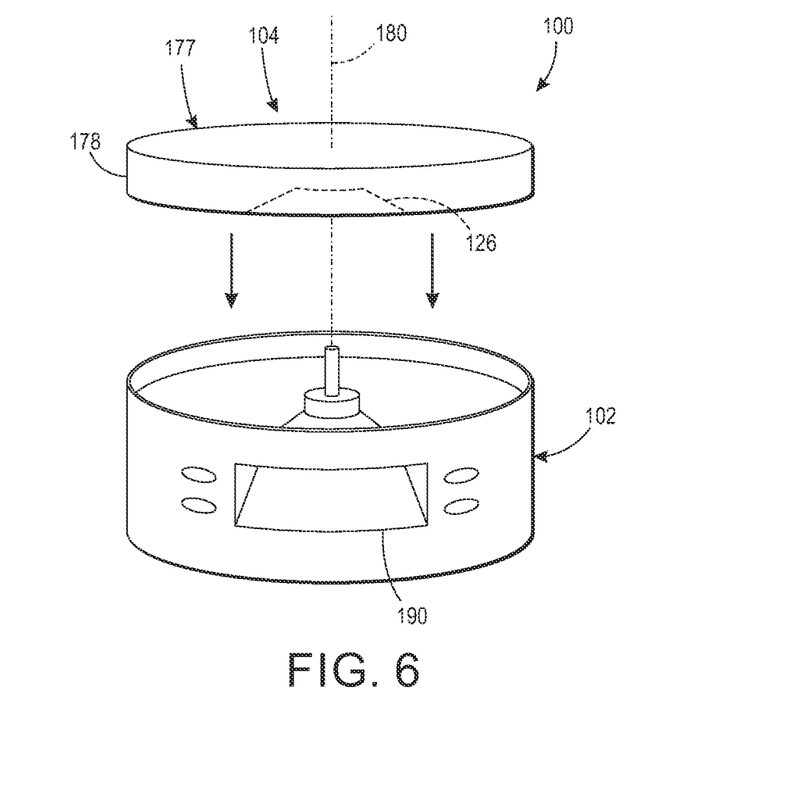
FIG. 6 is a schematic exploded representation of an example of the apparatus in FIG. 1; and, FIG. 7 is a schematic cross-sectional view of the example apparatus in FIG. 6.

FIG. 6 is a schematic exploded representation of an example of the apparatus in FIG. 1.

Figure 7:
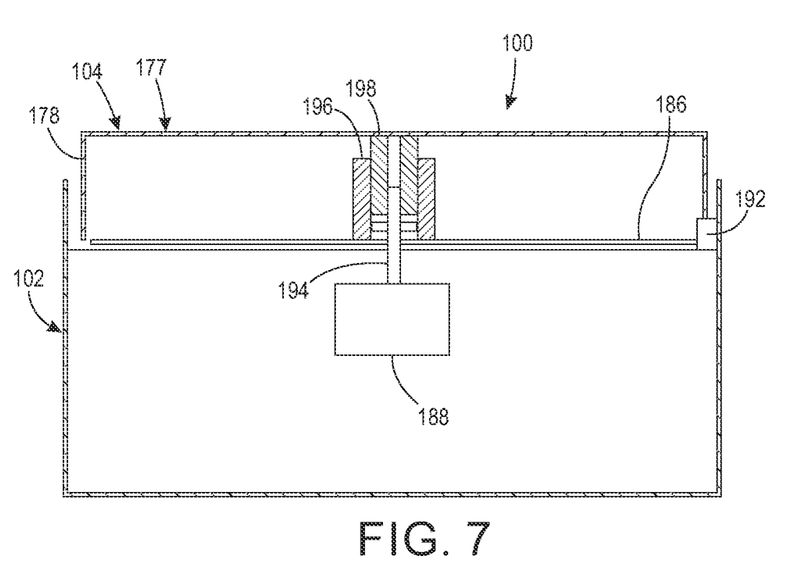

FIG. 7 is a schematic cross-sectional view of the example apparatus in FIG. 6. The following should be viewed in light of FIGS. 1 through 7. In an example embodiment, cassette 104 includes body 177 with rigid outer cylindrical wall 178, central axis 180, radial walls 182 separating the compartments. However, it should be understood that other shapes and configurations are possible for cassette 104. Cassette 104 can be a one piece plastic molding and can either be transparent or opaque. In the example of FIGS. 2 and 3, eight compartments are shown; however, it should be understood that cassette 104 is not limited to any particular number of compartments and that other numbers of compartments are possible. In an example embodiment, cassette 104 includes 30 compartments to enable extractions of medications (four compartments daily) for up to one week leaving one or more reserve compartments. Outside diameter 184 can be selected according to the configuration and size of element 102 or as needed to provide the desired number and size of compartments 120. For example, a range of 6 to 8 inches for 184 enables sufficient capacity per compartment to store multiple pills and capsules.

In an example embodiment, port 126 is an opening in lid 186 of the cassette. The lid is attached to the body and is rotatable about central axis 180 using actuator 188, which can be any actuator known in the art. The lid also can be a molded plastic part and port 126 an aperture corresponding to the size and shape of one compartment 120. Thus, when lid 186 is rotated to align port/aperture 126 with a compartment, all the pills in the compartment fall out of the compartment by gravitational force into dispensing port 190. Cassette 104 can be shipped so that port/aperture 126 is locked into position corresponding to an empty reserve compartment, for example by anti-rotation feature 192. When the cassette is installed in dispensing device 102 and has been confirmed as being a correct cassette, the locking of the lid is removed and at the appropriate time, actuator 188 rotates the lid to align with the appropriate compartment 120.

In an example embodiment, dispenser 102 includes lid drive gear shaft 194, lid 186 includes hub 196, and body 177 includes hub 198. Hubs 196 and 198 enable relative rotation of the lid and body 177.

The following provides further detail regarding apparatus 100, system 200, and flow chart 300. Advantageously, service entity 204 and computer 202 are able to integrate and synchronize various prescriptions for a patient. For example, the prescriptions may originate from different health care providers who may not be in communication with each other or even aware that other medications being prescribed by other health care providers. For example, computer 202 receives prescriptions 224 and 230 and sends the prescriptions to the pharmacy entity for fulfillment. Thus, all the prescriptions for the patient are integrated by computer 202. Pharmacy entity 214 is able to preload cassette 104 with the respective dosages of the medications included in prescriptions 224 and 230 and deliver the preloaded cassette according to a schedule that can be established and adjusted as needed by the patient. Preloaded cassette 104 also can be picked up at a location for the pharmacy entity.

Advantageously, the preloading of the cassette eliminates the problems noted above regarding incorrect loading of a dispenser due to the patient or other person manually loading medications into a dispenser. Further, sealing the compartments in cassette 104 makes the cassette child-proof and reduces the possibility of the patient or other person accessing the compartments and possibly removing or adding medications such that the medications in the compartment are no longer in compliance with the medication regimen for the patient. Dispensing element 102 extracts pills from the appropriate compartment at the appropriate time.

Apparatus 100, for example, cassette 104 and/or computer 170 provide embedded intelligence. For example, identification element 128 can include a unique bar code identifier, such as a quick response code, radio frequency identification, a near field communication (NFC) tag or any similar device known in the art. Apparatus 100 is locally or remotely programmable to access and recognize element 128 as noted above. Thus, element 102 can determine whether a particular cassette has been installed into the correct dispenser and contains the correct medications. As noted above, when an incorrect cassette is detected, dispenser element 102, for example, computer 170, transmits alarm signal 132 and implements sensory alarm signal 136. Entity 202 and/or monitoring service 134 can notify the patient, a caregiver for the patient, and/or the pharmacy entity to rectify the situation.

Also as noted above, element 102 can block extraction of medications from an incorrect cassette.

Advantageously, apparatus 100 provides an intuitive interface for the patient. For example, apparatus 100 can include user interface 190 including a touch screen able to implement enable typical computer interface functions, speech synthesis, and speech recognition. In an example embodiment, apparatus 100 provides a communication link between a patient and a remote caregiver or monitoring service 134.

As noted above, blister pack configurations may not be ergonomically optimal for patient use. Advantageously, apparatus 100 does not require the patient or caregiver to read labels and manipulate a blister pack. Instead, pills, such as pills 122 and 162, are dropped into a cup or other container that is easily accessed by the patient or caregiver.

Communication among apparatus 100 and entities 204, 214, and 222/228 can be by any means known in the art including hardwired communications or radio-frequency communications.

To enhance medication adherence, element 102 reliably indexes cassette 104 to the appropriate compartment 120 at the appropriate time and dispenses the appropriate medication at the appropriate dosages. Apparatus 100 communicates faults or anomalies back to monitoring service 134, the patient, and/or a caregiver. The faults or anomalies include, but are not limited to:

1. Incorrect cassette: information 130 for the cassette does not match prescription information 106—transmit alarm signal 132 to monitoring service 134/caregiver/patient.
2. Scheduled dosage not in compliance with medication regimen due to a dosage being extracted at a time other than the scheduled time according to information 106 or due to extraction of an as-needed medication—transmit message 144 to monitoring service 134/caregiver/patient.
3. Cassette 104 has not been installed in dispensing element 102 by point in time 166—transmit warning signal 168 to monitoring service 134/caregiver.
4. Medication has been extracted by but not removed from the dispensing device—transmit signal 169 to monitoring service 134/caregiver/patient.

Advantageously, apparatus 100 provides the patient and/or caregiver flexible exception handling in the event normal routines do not apply. For example, a 'pre-dispense' or 'post-dispense' function can be enabled to dispense one or more doses early or late if the patient plans to be unavailable at the scheduled dosage time. In an example embodiment, input 140 can be used to signal exception handling and time interval 142 can be used to provide the time before or after the scheduled dosage for the exception handling.

In an example embodiment, user interface 190 provides a prompt to remove an empty cassette and install a new/full one. In an example embodiment, cassette 104 is loaded so that lid 186 and port 126 are facing downward. The port is located above a user access point for dispensed medications. Actuator 188 rotates lid 186 or body 177 to unlock the cassette. In an example embodiment, actuator 188 rotates body 177 to move the next compartment 120 in line with port 126. In an example embodiment, actuator 188 rotates lid 186 to move the next compartment 120 in line with port 126. Thus, pills from successive compartments fall out as they are aligned with the aperture.

In the example of FIGS. 4 and 5, service entity 204 receives annuity streams from both apparatus 100 and from the medication packaging and delivery performed by entity 214. For example, payer 302 could sponsor the process shown in FIGS. 4 and 5. Another potential sponsor may be a hospital or other entity providing health care services. For example, to lower re-admittance rates (increase medication adherence), discharged patients can be provided apparatus 100 and the service depicted in FIGS. 4 and 5.

From an environment perspective, cassettes 104 can be reusable, eliminating or reducing packaging waste streams. From a security perspective, cassette-based distribution provides versatility in tracking of medications, particularly any narcotic or controlled substances. For example, each cassette can easily be provided with its own passive or active identifier.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus for dispensing medications, comprising:
a dispensing device configured to store first prescription information including: an identification of each first medication included in a first plurality of medications; a respective dosage for said each first medication; and a first plurality of time spans, including first respective points in time, for dispensing the first plurality of medications; and,
a cassette:
installed in the dispensing device;
including a first plurality of sealed compartments, each first compartment in the first plurality of sealed compartments storing at least one first respective pill for each medication in a second plurality of medications; and,
including an identification element storing second prescription information regarding the second plurality of medications; and,
at least one dispensing port, wherein:
the dispensing device is configured to:
compare the first and second prescription information to determine if the second plurality of medications is in compliance with the first prescription information; and,
within each first time span in the first plurality of time spans and when the second plurality of medications is in compliance with the first prescription information:
access said each first compartment via the at least one dispensing port; and,
extract every at least one first pill from said each first compartment; and,
sealing of the first plurality of sealed compartments prevents access to said each first compartment except through the at least one dispensing port.

2. The apparatus of claim 1, wherein:
the dispensing device is configured to:
determine, using the first and second prescription information, whether the second plurality of medications is the same as the first plurality of medications; and,
within said each first time span in the first plurality of time spans, and when the second plurality of medications is the same as the first plurality of medications:
access said each first compartment via the at least one dispensing port; and,
extract the every at least one first pill from said each first compartment.

3. The apparatus of claim 2, wherein when the dispensing device determines that the second plurality of medications is not the same as the first plurality of medications or is not in compliance with the first prescription information, the dispenser is configured to:
block extraction of the at least one first pill from the first compartment;
transmit an alarm signal; and,
implement a sensory alarm signal.

4. The apparatus of claim 1, wherein:
the first prescription information includes instructions to extract the every at least one first pill from a second compartment in the first plurality of sealed compartments within a second time span in the first plurality of time spans; and,
the dispensing device is configured to:
receive an input; and,
in response to the input:
abort, within the second time span, dispensing of the every at least one first pill from the second compartment; and,
extract the every at least one first pill from the second compartment prior to or after the second time span.

5. The apparatus of claim 1, wherein the dispensing device includes:
a memory element configured to store computer readable instructions and the first prescription information; and,
a processor configured to execute the computer readable instructions to, within each first time span in the first plurality of time spans, and when the second plurality of medications is in compliance with the first prescription information:
access using the dispenser, said each first compartment via the at least one dispensing port; and,
extract, using the dispenser, every at least one first pill from said each first compartment.

6. A method for dispensing medications, comprising:
storing in a dispensing device first prescription information including: a respective identification of each first medication included in a first plurality of medications; respective dosages for said each first medication; and first plurality of time spans, including first respective points in time, for dispensing the first plurality of medications;
placing, in each first compartment in a first plurality of compartments for a cassette, at least one first respective pill for each medication in a second plurality of medications;
storing, in an identification element affixed to the cassette, second prescription information regarding the second plurality of medications;
sealing the first plurality of compartments;
blocking access to said each first compartment except through at least one dispensing port;
installing the cassette in the dispensing device;
comparing, using the cassette, the first and second prescription information to determine if the second plurality of medications is in compliance with the first prescription information;
within each first time span in the first plurality of time spans and when the second plurality of medications is in compliance with the first prescription information:
accessing, using the dispensing device, said each first compartment via the at least one dispensing port; and,
extracting, using the dispensing device, every at least one first pill from said each first compartment.

7. The method of claim 6, further comprising:
determining, using the dispensing device and the first and second prescription information, whether the second plurality of medications is the same as the first plurality of medication; and,
within said each first time span in the first plurality of time spans, and when the second plurality of medications is the same as the first plurality of medications:
accessing, using the dispensing device, said each first compartment via the at least one dispensing port; and,
extracting, using the dispensing device, every at least one first pill from said each first compartment.

8. The method of claim 7, further comprising:
determining, using the dispensing device and the first and second prescription information, that the second plurality of medications is not the same as the first plurality of medications or is not in compliance with the first prescription information;
blocking, using the dispensing device, extraction of the at least one first pill from the first compartment;
transmitting, using the dispensing device, an alarm signal; and,
implementing, using the dispensing device a sensory alarm signal.

9. The method of claim 6, wherein the first prescription information includes instructions to extract the every at least one first pill from a second compartment in the first plurality of sealed compartments within a second time span in the first plurality of time spans, the method further comprising:
receiving an input using the dispensing device; and,
for the second compartment and in response to the input:
aborting, using the dispensing device and at the second point in time, extraction of the every at least one first pill within the second time span; and,
extracting, using the dispensing device, the every at least one first pill from the second compartment prior to or after the second time span.

10. The method of claim 9, wherein the input includes a time interval, the method further comprising:
extracting, using the dispensing device, the every at least one first pill in the second compartment prior, by the time interval, to the second time span; or,
extracting, using the dispensing device, the every at least one first pill in the second compartment after, by the time interval, the second time span.

11. The method of claim 6, further comprising:
storing, in a memory element in the dispensing device, computer readable instructions and the first prescription instructions; and,
executing, using a processor in the dispensing device, the computer readable instructions to, within said each first time span in the first plurality of time spans and when the second plurality of medications is in compliance with the first prescription information:
access, using the dispensing device, said each first compartment via the at least one dispensing port; and,
extract, using the dispensing device, the every at least one first pill from said each first compartment.

12. A computer-based system for dispensing medications, comprising:
a first computer, operated by or for a service entity, including a first processor and a first memory element configured to store first computer readable instructions;
a second computer, operated by or for a pharmacy entity separate from the service entity, including a second processor and a second memory element configured to store second computer readable instructions; and,
a dispensing apparatus remotely located from the service entity and the pharmacy entity and including a dispensing device including a third computer with a third processor and a third memory element configured to store third computer readable instructions, wherein:
the first processor is configured to execute the first computer readable instructions to:
receive, from at least one first health care provider, a first plurality of prescriptions for a first plurality of medications, each prescription in the first plurality of prescriptions including: an identification of a first respective medication; a respective dosage for the first respective medication; and a first plurality of time spans, including first respective points in time, for dispensing the first plurality of medications; and,
transmit to the second computer:
the first plurality of prescriptions; and,
instructions to place in each first compartment of a first plurality of compartments for a cassette, installable in the dispensing device, the first plurality of medications;
the dispensing apparatus includes:
the cassette:
installed in the dispensing device, with the at least one first respective pill for each second medication included in a second plurality of medications; and,
including an identification element configured to store information regarding the second plurality of medications;
at least one dispensing port;
the cassette is sealed to block access to said each first compartment except through the at least one dispensing port; and,
the third processor is configured to execute the third computer readable instructions to:
receive the first plurality of prescriptions;
compare the first plurality of prescription information and the information regarding the second plurality of medications to determine if the second plurality of medications is in compliance with the first prescription information; and,
within each first time span in the first plurality of time spans, and when the second plurality of medications is in compliance with the first plurality of prescriptions:
access, using the dispensing device, said each first compartment via the at least one dispensing port; and,
extract, using the dispensing device, every at least one first pill from said each first compartment.

13. The computer-based system of claim 12, wherein the first computer is configured to transmit the first plurality of prescriptions to the third computer.

14. The computer-based system of claim 12, wherein:
the third processor is configured to execute the third computer readable instructions to:
determine, using the first plurality of prescriptions and the information, whether the second plurality of medications is the same as the first plurality of medications; and,
within said each first time span in the first plurality of time spans, and when the second plurality of medications is the same as the first plurality of medications:
access said each first compartment via the at least one dispensing port; and, extract the every at least one first pill from said each first compartment.

15. The computer-based system of claim 12, wherein:
the cassette includes an identification element storing information regarding the second plurality of medications; and,
the third processor is configured to execute the third computer readable instructions to:
  determine, using the first plurality of prescriptions and the information, that the second plurality of medications is not the same as the first plurality of medications or is not in compliance with the first plurality of prescriptions;
  block extraction, using the dispensing element, of the at least one first pill from the first compartment;
  transmit an alarm signal; and,
  implement a sensory alarm signal.

16. The computer-based system of claim 12, wherein the at least one first health care provider includes a plurality of health care providers.

17. The computer-based system of claim 12, wherein:
the first plurality of prescriptions includes instructions to extract the every at least one first pill from a second compartment in the first plurality of sealed compartments within a second time span in the first plurality of time spans; and,
the dispensing device is configured to:
  receive an input; and,
  in response to the input:
    abort, within the second time span, dispensing of the every at least one first pill from the second compartment; and,
    extract the every at least one first pill from the second compartment prior to or after the second time span.

18. The computer-based system of claim 17, wherein:
the input includes a time interval; and,
the third processor is configured to execute the third computer readable instructions to:
  extract, using the dispensing device, the every at least one first pill in the second compartment prior, by the time interval, to the second time span; or,
  extract, using the dispensing device, the every at least one first pill in the second compartment after, by the time interval, the second time span.

19. The computer-based system of claim 12, wherein the first computer is configured to transmit the information regarding the second plurality of medications to the third computer.

20. A computer-based method for dispensing medications, comprising:
storing, in a first memory element of a first computer, operated by or for a service entity, first computer readable instructions;
executing, using a first processor the first computer readable instructions to:
  receive, from at least one first health care provider, a first plurality of prescriptions for a first plurality of medications, each prescription in the first plurality of prescriptions including: an identification of a first respective medication included in the first plurality of medications; a respective dosage for the first respective medication; and a first plurality of time spans, including first respective points in time, for dispensing the first respective medication; and,
  transmit to a second computer, operated for or by a pharmacy entity separate from the service entity:
    the first plurality of prescriptions; and,
    instructions to place in each first compartment of a first plurality of compartments for a cassette, installable in the dispensing device, the first plurality of medications;
placing, at a facility operated by or for the pharmacy entity, in each first compartment in a first plurality of compartments for a cassette, at least one first respective pill for each second medication in a second plurality of medications;
storing, in an identification element affixed to the cassette, information regarding the second plurality of medications;
sealing the cassette to block access to said each first compartment except through at least one dispensing port;
installing, in a dispensing apparatus including a third computer with a third processor and third memory element, the cassette, with the at least one first respective pill for each second medication present in said each first compartment;
storing third computer readable instructions in the third memory element;
executing, using the third processor, the third computer readable instructions to:
  receive the first plurality of prescriptions;
  compare the first plurality of prescription information and the information regarding the second plurality of medications to determine if the second plurality of medications is in compliance with the first prescription information; and,
  within each first time span in the first plurality of time spans, and when the second plurality of medications is in compliance with the first plurality of prescriptions:
    access, using a dispensing device included in the dispensing apparatus, said each first compartment via the at least one dispensing port; and,
    extract, using the dispensing device, every at least one first pill from said each first compartment.

21. The computer-based method of claim 20, wherein the first computer is configured to transmit the first plurality of prescriptions to the third computer.

22. The computer-based method of claim 20, further comprising:
executing, using the third processor, the third computer readable instructions to:
  determine, using the first plurality of prescriptions and the prescription information, whether the second plurality of medications is the same as the first plurality of medications; and,
  at said each first time span in the first plurality of time spans, and when the second plurality of medications is the same as the first plurality of medications:
    access said each first compartment via the at least one dispensing port; and,
    extract the every at least one first pill from said each first compartment.

23. The computer-based method of claim 20, further comprising:
storing in an identification element affixed to the cassette, prescription information regarding the second plurality of medications; and,
executing, using the third processor, the third computer readable instructions to:
  determine, using the first plurality of prescriptions and the prescription information, that the second plurality of medications is not the same as the first plurality of medications or is not in compliance with the first plurality of prescriptions;
block extraction, using the dispensing element, of the at least one first pill from the first compartment;
transmit an alarm signal; and,
implement a sensory alarm signal.

24. The computer-based method of claim 20, wherein the at least one first health care provider includes a plurality of health care providers.

25. The computer-based method of claim 20, wherein:
the first plurality of prescriptions includes instructions to extract the every at least one first pill from a second compartment in the first plurality of sealed compartments within a second time span in the first plurality of time spans; and,
the third processor is configured to execute the third computer readable instructions to:
extract, using the dispensing device, the every at least one first pill from a second compartment in the first plurality of compartments within a second time span in the first plurality of time spans;
receive an input; and,
in response to the input:
abort, within the second time span, dispensing the every at least one first pill from the second compartment; and,
extract the every at least one first pill from the second compartment prior to or after the second time span.

26. The computer-based method of claim 25, wherein:
the input includes a time interval; and,
the second processor is configured to execute the second computer readable instructions to:
extract, using the dispensing device, the every at least one first pill in the first compartment prior, by the time interval, to the second time span; or,
extract, using the dispensing device, the every at least one first pill in the first compartment after, by the time interval, the second time span.

27. The computer-based method of claim 20, wherein the first computer is configured to transmit the information regarding the second plurality of medications to the third computer.

* * * * *